(12) United States Patent
Mossoba et al.

(10) Patent No.: US 8,652,801 B2
(45) Date of Patent: Feb. 18, 2014

(54) HYDROPHILIC IR TRANSPARENT MEMBRANE, SPECTROSCOPIC SAMPLE HOLDER COMPRISING SAME AND METHOD OF USING SAME

(75) Inventors: Magdi Mossoba, Great Falls, VA (US); Sufian Al-Khaldi, Bowie, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 0 days.

(21) Appl. No.: 13/584,208

(22) Filed: Aug. 13, 2012

(65) Prior Publication Data

US 2012/0301917 A1   Nov. 29, 2012

Related U.S. Application Data

(60) Division of application No. 12/150,048, filed on Apr. 23, 2008, now Pat. No. 8,263,360, which is a continuation of application No. 11/343,561, filed on Jan. 30, 2006, now abandoned.

(51) Int. Cl.
| | | |
|---|---|---|
| C12Q 1/06 | (2006.01) | |
| C12M 1/00 | (2006.01) | |
| G03G 5/16 | (2006.01) | |
| C08F 110/00 | (2006.01) | |
| C12Q 1/02 | (2006.01) | |
| C12Q 1/04 | (2006.01) | |
| C12Q 1/10 | (2006.01) | |
| C08F 236/00 | (2006.01) | |
| C08F 236/02 | (2006.01) | |
| C08F 110/04 | (2006.01) | |

(52) U.S. Cl.
USPC .............. 435/38; 250/316.1; 435/29; 435/34; 435/283.1; 521/143; 521/148

(58) Field of Classification Search
None
See application file for complete search history.

(56) References Cited

U.S. PATENT DOCUMENTS

| | | |
|---|---|---|
| 3,309,299 A | 3/1967 | Mantell |
| 5,439,736 A | 8/1995 | Nomura |
| 5,470,757 A | 11/1995 | Gagnon et al. |
| 5,733,507 A | 3/1998 | Zakim |
| 5,764,355 A | 6/1998 | Gagnon et al. |
| 5,786,226 A | 7/1998 | Bocker et al. |
| 5,848,977 A | 12/1998 | Zakim et al. |
| 5,939,314 A | 8/1999 | Koontz |
| 5,985,475 A | 11/1999 | Reynolds et al. |
| 6,375,545 B1 | 4/2002 | Yano et al. |
| 6,531,702 B1 | 3/2003 | Mischler et al. |
| 6,878,419 B2 | 4/2005 | David et al. |

OTHER PUBLICATIONS

"Recovery of *Enterobacter sakazakii* and *Klebsiella pneumonia* from Infant Formula Milk by Filtration and Cultivation on a Unique Infrared-Transparent Hydrophilic Membrane Filter", (M.M. Mossoba et al), Abstract for poster at the FDA Science Forum in Washington DC, (Apr. 27-28, 2005).

Liu and Wang. 1996 Surface Modification of Bio-Carrier by Plasma Oxidation-Ferric Ions Coating Technique to Enhance Bacterial Adhesion, Environ. Sci. Health, vol. A31, No. 4, pp. 869-879.

Mossoba et al. 2002. "Novel Application of a Disposable Optical Film to the Analysis of Bacterial Strains: A chemometric Classification of Mid-Infrared Spectra." Applied Spectroscopy, vol. 56, No. 6, pp. 732-736.

Mossoba et al. 2003, "Application of a disposable transparent filtration membrane to the infrared spactroscopie discrimination among bacterial species" Journal of Microbiological Methods, vol. 55, pp. 311-314.

Iverson et al. 2004 Isolation of *Enterobacter sakazakii* and other Enterobactriaceae from powdered infant formula milk and related products. Food Microbiology, vol. 21, pp. 771-777.

*Primary Examiner* — Jon P Weber
*Assistant Examiner* — Kailash C Srivastava
(74) *Attorney, Agent, or Firm* — Edwards Wildman Palmer LLP; Peter F. Corless; Richard B. Emmons

(57) ABSTRACT

The present invention features hydrophilic IR-transparent porous membranes, particularly hydrophilic IR-transparent porous polyethylene membranes and methods of preparing the hydrophilic membranes by treatment of hydrophobic IR-transparent porous membranes with plasma. The present invention further features spectroscopic sample holders which incorporate the hydrophilic IR-transparent porous membranes and methods of identifying bacteria and other microorganisms in samples by infrared spectroscopy.

6 Claims, 6 Drawing Sheets

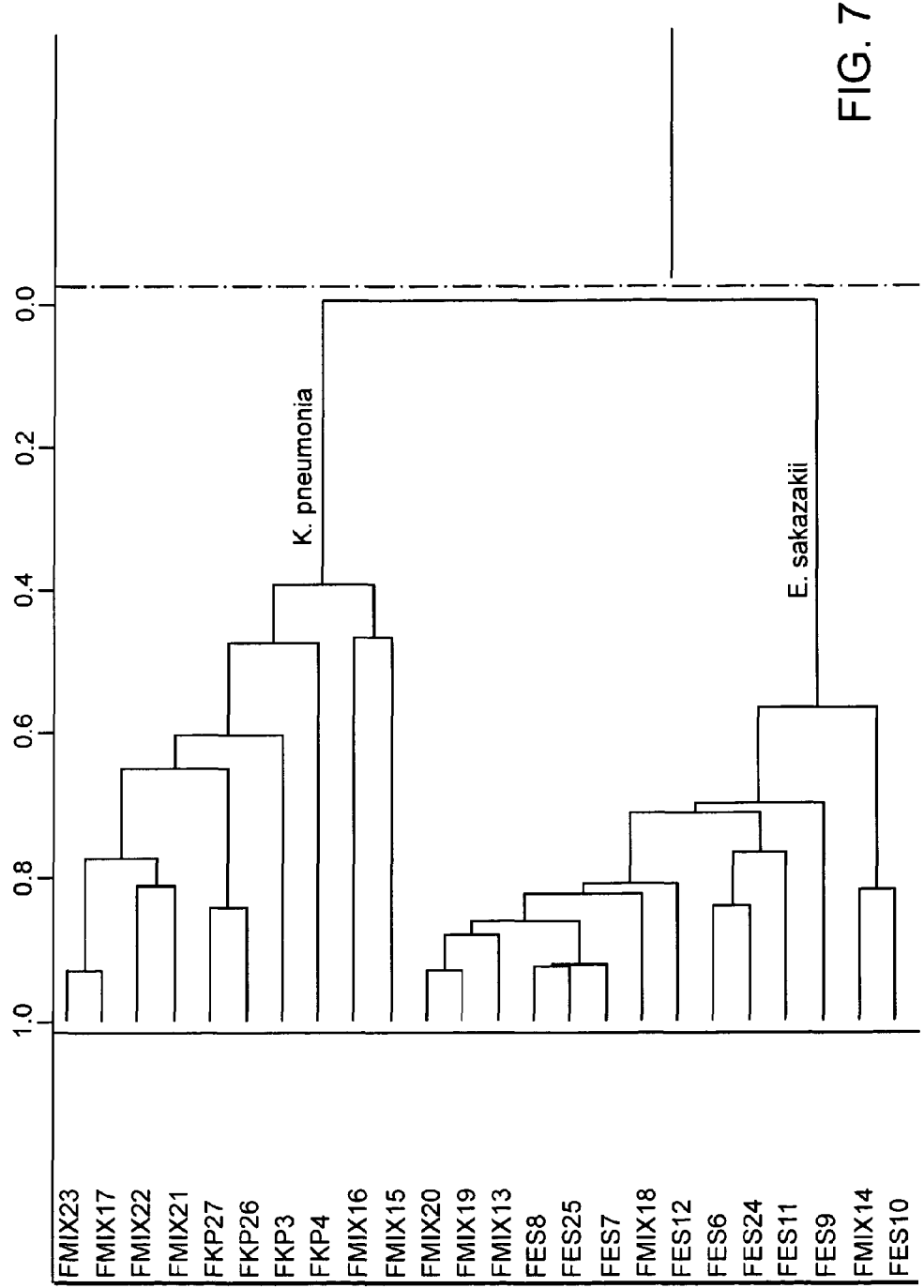

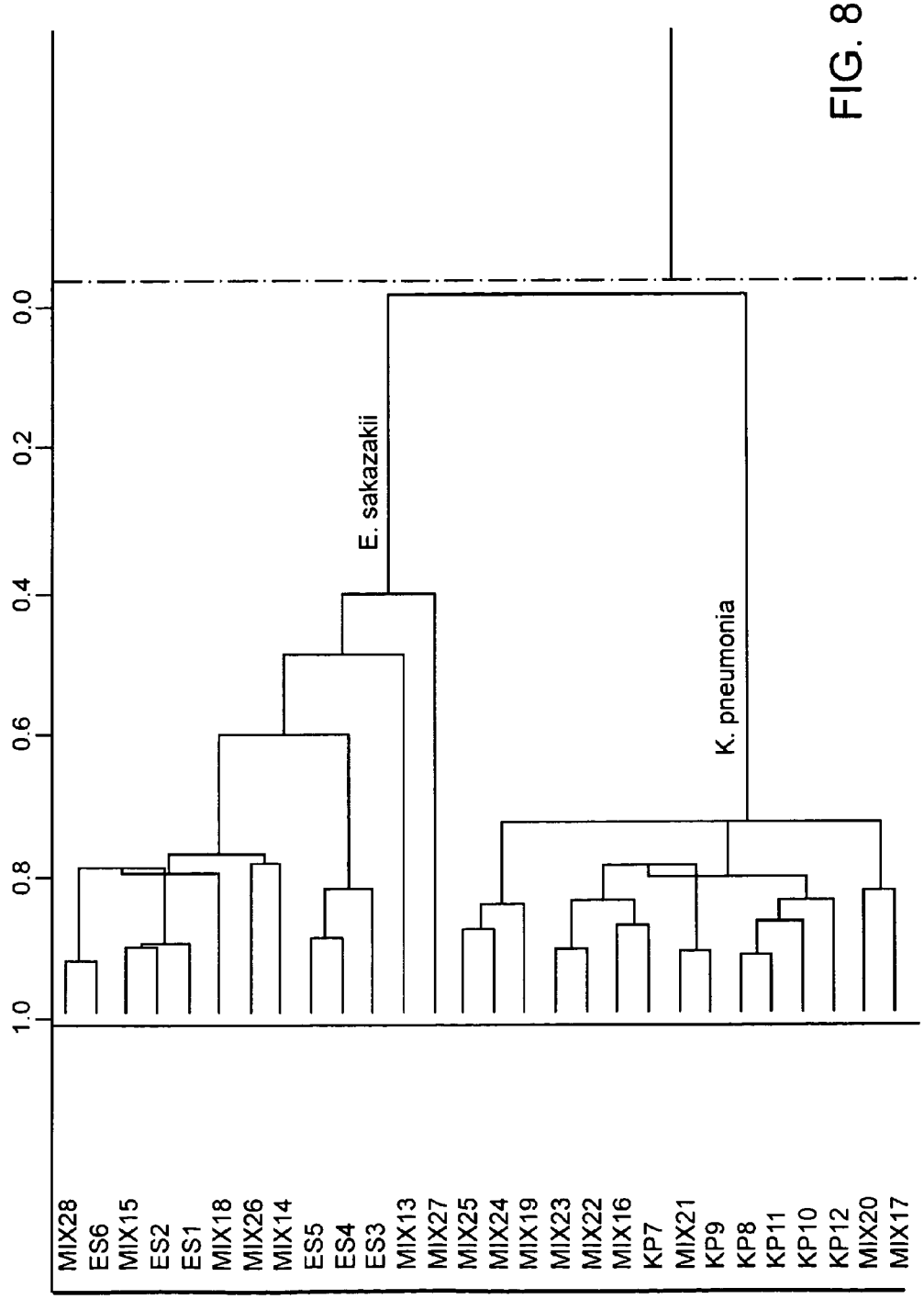

HYDROPHILIC IR TRANSPARENT MEMBRANE, SPECTROSCOPIC SAMPLE HOLDER COMPRISING SAME AND METHOD OF USING SAME

RELATED APPLICATIONS

This application is a divisional of U.S. patent application Ser. No.: 12/150,048 filed Apr. 23, 2008 which is a continuation of U.S. patent application Ser. No.: 11/343,561 filed Jan. 30, 2006. The entire contents of each of the aforementioned applications is expressly incorporated herein by reference in their entireties.

BACKGROUND OF THE INVENTION

1. Field of the Invention

The present invention provides hydrophilic IR-transparent microporous membranes, methods of making said membranes by treatment of hydrophobic microporous membranes with plasma, spectroscopic sample holders composed of the hydrophilic IR-transparent microporous membranes and methods of using the hydrophilic IR-transparent microporous membranes. More particularly, the present invention provides hydrophilic IR-transparent microporous membranes and methods of using said membranes to identify bacterial impurities in food using infrared spectroscopy.

2. Background

In infrared ("IR") spectroscopy, a beam of light from an infrared source is passed through a sample. The light that is transmitted through the sample is evaluated in comparison with the incident light and its intensity plotted as a function of wavelength or wavenumber. Wavenumber is expressed herein as centimeters$^{-1}$ or "cm$^{-1}$". This spectral plot or spectrum can provide information regarding the functional groups and structural features of the sample and, accordingly, IR spectroscopy has become a valuable tool in analytical chemistry for certain types of samples.

The infrared region of the electromagnetic spectrum extends from the upper end of the visible region (wavenumber of approximately 14,300 cm$^{-1}$) to the microwave region (near 20 cm$^{-1}$). The region which is typically of most interest to analytical chemists for determination of structural features of an organic sample is from about 4000 cm$^{-1}$ to about 400 cm$^{-1}$. In this region of the spectrum, organic compounds absorb incident infrared light at frequencies corresponding to the vibrational frequencies of the compound. These absorbed frequencies are characteristic of the structural features of the compound or compounds in the sample and can permit rapid identification. The intensities of the peaks in the spectral plot or spectrum are a function of the concentration of the sample, extinction coefficient, and path length of the incident light through the sample.

To obtain an infrared spectrum of a sample, the sample is typically applied to a sample holder or "cell". This sample holder or cell holds the sample in the path of the incident beam of infrared light. It is essential that the material used for the sample holder be highly transmissive in that region of the IR spectrum which is of interest. Also, the sample holder should not be soluble in, or reactive with, either the sample or solvent (if any). Illustrative examples of materials used in sample holders include inorganic salts, glasses, and quartz.

Sodium chloride (NaCl) is perhaps the most commonly used material since it does not absorb infrared light in the range of 4000 to 625 cm$^{-1}$ and is relatively less expensive than some alternatives. However, NaCl crystals are very susceptible to moisture and easily broken. For a discussion of cell materials see Pasto and Johnson, Organic Structure Determination, Prentice-Hall, Inc., 1969, pp. 145-147.

In the majority of analyses, the holder (or cell) is a pair of plates made from crystals of an inorganic salt that has been precisely machined and polished for maximum optical clarity. A sample is then placed between the pair of plates and mounted by a variety of techniques in the beam of infrared light. Solid samples are often ground and intimately mixed with an inorganic salt such as potassium bromide, pressed into a thin wafer or pellet, applied to a sample holder, and mounted in the infrared beam. Alternatively, samples may be mulled with an oil such as NUJOL™ mineral oil, applied to a sample holder, and analyzed as a thin film. Liquid samples, either neat or in solvent, may also be analyzed using a sealed cell in which a pair of plates are sealed together with a spacer to provide a chamber in which the sample is held. In addition to the use of plates, other sample preparation techniques have been developed. For instance, liquids or solutions having a relatively high surface tension such as aqueous solutions have been analyzed by suspending a thin film from a loop of wire. Also, a solution may be coated and dried to form a film, e.g., a solution may be coated on a film of polytetrafluoroethylene and dried, and the resulting thin film peeled from the polytetrafluoroethylene and analyzed.

Due to the susceptibility of many known cell materials to degradation by moisture and the long drying time necessary for preparation of some samples, analysis of aqueous samples is difficult. Increasingly stringent regulations have prompted many industries to reduce or eliminate organic solvent use and emissions, prompting the development of water-based processes and products. Illustrative examples of materials that have been used for cells for use with aqueous samples include silver bromide, calcium fluoride, and barium fluoride. Use of such materials is limited by the typically high expense, limited useful spectral ranges, burdensome maintenance, and difficult sample preparation associated with such materials. Typically, aqueous samples are analyzed using a horizontal attenuated total reflectance ("ATR") crystal to which a sample is applied. A beam of infrared light is reflected repeatedly through the sample before being evaluated in a detector. Use of this technique is hampered by the high cost of sample holders and difficulties encountered in sample preparation and maintenance. In part due to these problems, IR spectroscopy has not reached its potential as a routine tool for analysis of aqueous samples.

In addition to the problems described, namely cost, sensitivity to moisture and fragility, commercially available cells have high maintenance requirements. In view of the high costs, disposal of these cells is prohibitive. Accordingly, sample holders must be carefully cleaned, typically with organic solvents, after each analysis to prevent contamination from one sample to the next. In some instances, the solvents may present health risks to operators. In addition, the high cost of sample holders tends to inhibit retention of samples on a long term basis.

Dove and Hallett, Chemistry and Industry, 1966, pp. 2051-53, describe an all-plastic evacuable cell to be used for infrared or ultraviolet spectroscopic analysis of gases. The cell has windows that can be made from RIGIDEX™ Type 35 polyethylene. The relative thickness of the windows, i.e., about 3 millimeters, would preclude the use of such sample holders in most routine IR spectroscopic analysis due to the strong absorbances. Andrede, J.Chem. Ed., 66(10), p. 865, 1989, describes using polyethylene film as windows in a sample cell. For sampling of liquids the author suggests applying the sample to a film stretched over a ring, covering the sample with a second film, and securing both stretched films with a second ring.

Gagnon, U.S. Pat. No. 5,470,757, describes hydrophobic microporous polymeric membranes and the use of same as sample holders for IR spectroscopy. More particularly, Gagnon teaches that solid (e.g., in powder form), liquid and solution samples can be supported by the recited hydrophobic microporous polymeric membranes such that the IR spectrum of the sample. The hydrophobic microporous polymeric membranes are easy to use and inexpensive to use. Unfortunately, these to membranes are not well suited for use with aqueous samples due to the hydrophobicity of the membranes.

*Enterobacter sakazakii* is a Gram-negative rod shaped bacterium that has been associated with neonate deaths and outbreaks of a rare form of infant meningitis and other diseases (*Med Baltimore* (2001) 80 (1):113-122). Reported case-mortality rates were high and ranged from 40-80% among immunocompromised infants (*J Food Protection* (1997) 60 (3): 226-230). Although the mode of transmission of this organism has not been identified, the presence of *E. sakazakii* in powdered infant formula milk (IFM) has been of particular concern (*J Am Med Assoc* (2001) 287:2204-2205). Literature surveys indicate that the incidence of *E. sakazakii* in IFM commercial products is low, namely 20 out of 141, 8 out of 120 (*J Food Protection* (1997) 60 (3):226-230), and 2 out of 82 IFM (Iverson and Forsythe 2004), and its isolation levels range from 0.36 to 66.0 cells/100 g (*J Clin Microbiol* (1998) 26 (4):743-6).

Established conventional procedures (*Food Microbiol* (2004) 21:771-777; *J Clin Microbiol* (1998) 26 (4):743-6; and *J Food Protection* (1997) 60 (3):226-230) for the isolation of *E. sakazakii* from dehydrated powdered infant formula include the 2002 FDA culture method (see, URL:http://www.cfsan.fda.gov/~comm/mmesakaz.html) which requires seven days. The FDA culture method entails pre-enrichment in distilled water, enrichment in Enterobacteriaceae enrichment broth, plating on violet red bile glucose agar, selecting five Enterobacteriaceae colonies and incubating on trypticase (tryptic) soy agar plates at 25° C. for 48-72 h to observe the yellow-pigmented colonies that are characteristic of *E. sakazakii*, and confirmation using the API 20E (bioMerieux, Inc, Hazelwood, Mo.) biochemical profiling system.

It would be desirable to develop faster, less expensive methods of identifying microorganism contaminants present in food samples. More particularly, it would be desirable to provide faster, less expensive methods of direct identification of harmful microorganism contaminants present in powdered foods including those contaminants present in powdered baby formula.

SUMMARY OF THE INVENTION

The present invention provides microporous hydrophilic polymeric membranes, particularly microporous hydrophilic polyethylene membranes, which is transparent to infrared radiation with a wavenumber of between about 1400 cm$^{-1}$ and about 750 cm$^{-1}$. The present invention further provides methods of making the microporous hydrophilic polymeric membranes by treatment of IR transparent microporous hydrophobic polymeric membranes with plasma.

The present invention further provides an infrared spectroscopy cell for use in direct detection of bacteria comprising a holder having a window; and a microporous hydrophilic polyethylene membrane situated in the window of the frame, wherein the microporous hydrophilic polyethylene membrane has a IR spectrum consisting essentially of absorption bands at 2918 and 2849 cm$^{-1}$, as well as two pairs of low intensity features near 1465 and 725 cm$^{-1}$.

In other embodiments, the present invention provides methods of assaying a test sample for bacteria by infrared spectroscopy, the method comprising the steps of contacting the test sample to a hydrophilic microporous polymeric membrane which is transparent to IR radiation having a wavenumber of between about 1400 cm$^{-1}$ and about 750 cm$^{-1}$;

incubating the hydrophilic microporous polymeric membrane after applying the test sample; and measuring a test IR spectrum after incubating the hydrophilic microporous polymeric membrane;

measuring a control IR spectrum of an IR-transparent microporous hydrophilic membrane which was not contacted with an aqueous test sample;

analyzing differences between the test IR spectrum and the control IR spectrum to determine the presence of bacteria in the aqueous test sample.

Preferred methods of identifying bacteria in samples provided by the present invention provide a rapid, reagent-free infrared (IR) microspectroscopic procedure that identify presumptive *E. sakazakii* colonies in less time than the current FDA approved method.

Other aspects of the invention are described infra.

BRIEF DESCRIPTION OF THE DRAWINGS

The invention will be further explained with reference to the drawing, wherein:

FIG. 7 is a dendogram plot illustrating successful differentiation of a mixture of colonies of *E. sakazakii* and *K. pneumonia* measured by IR microspectroscopy. The labels ES (*E. sakazakii*) and KP (*K. pneumonia*) represent microcolonies for test samples of each bacterium; each MIX label represents one colony from a test mixture that was presumptively identified as *E. sakazakii* or *K. pneumonia*; and FIG. 8 is a dendogram plot illustrating successful clustering of IR microspectroscopic data for colonies of *E. sakazakii* and *K. pneumonia* deposited by microarray printing onto the hydrophilic microporous polyethylene membrane. The labels ES (*E. sakazakii*) and KP (*K. pneumonia*) represent microcolonies for test samples of each bacterium; each MIX label represents one colony from a test mixture that was presumptively identified as *E. sakazakii* or *K. pneumonia*.

DETAILED DESCRIPTION OF THE INVENTION

Figure 1:
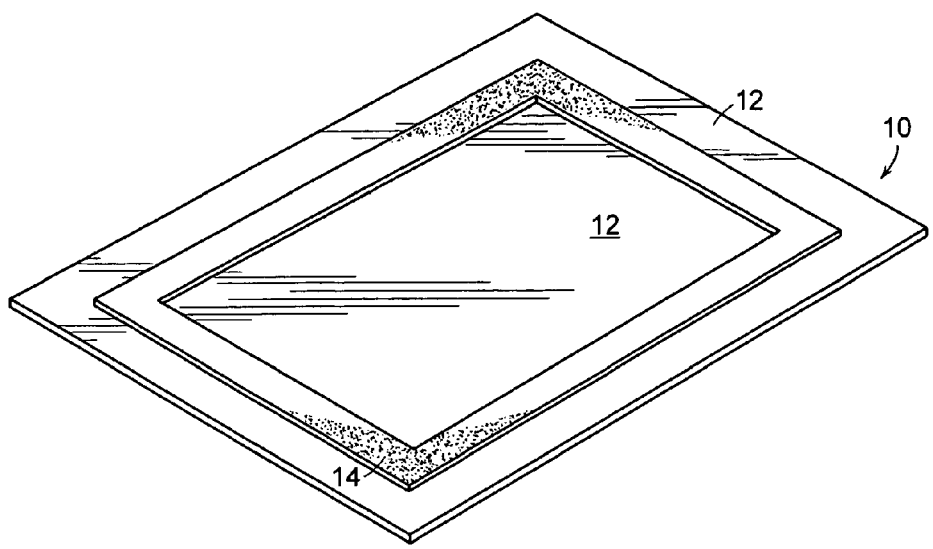
FIG. 1 is a plan view of one face of an illustrative embodiment of a sample holder of the invention.

The present invention provides hydrophilic microporous polymeric membranes which are substantially transparent to infrared radiation having a wavenumber of between about 1400 cm$^{-1}$ and about 750 cm$^{-1}$. Certain preferred hydrophilic microporous polyethylene membranes provided herein are substantially transparent to infrared radiation having a wavenumber of between about 4000 cm$^{-1}$ and about 3000 cm$^{-1}$, between about 2800 cm$^{-1}$ and about 1450 cm$^{-1}$ and between about 1400 cm$^{-1}$ and about 750 cm$^{-1}$. The hydrophilic microporous polymeric or polyethylene membranes provided herein are suitable for use as holders in infrared spectroscopy.

Certain microporous hydrophilic polyethylene membranes provided herein include those membranes which are transparent to infrared radiation with a wavenumber of between about 1400 cm$^{-1}$ and about 750 cm$^{-1}$. Certain other membranes provided herein are transparent to infrared radiation with a wavenumber of between about 4000 cm$^{-1}$ and about 3000 cm$^{-1}$, between about 2800 cm$^{-1}$ and about 1500 cm$^{-1}$ and/or between about 1450 cm$^{-1}$ and about 700 cm$^{-1}$. Certain microporous hydrophilic polyethylene membranes are substantially transparent to infrared radiation except for absorption bands of polyethylene which occur at between about 2918 to about 2849 cm$^{-1}$ (strong absorbance), at about 1465 cm$^{-1}$ (weak absorbance) and at about 725 cm$^{-1}$ (weak absorbance).

The term "substantially transparent" is intended to refer to materials which transmit at least about 90% of incident radiation, e.g., the material absorbs or reflects less than about 10% of the incident radiation. More preferably, "substantially transparent" is intended to refer to materials which transmit at least about 95% or about 99% of incident infrared radiation. In certain embodiments, substantially transparent membranes transmit at least 90%, 95% or 99% of incident radiation in a range of at least 100 cm$^{-1}$ or more preferably at least about 200 cm$^{-1}$ or about 300 cm$^{-1}$. For example, substantially transparent membranes for use in measuring bacterial colonies of *E. sakazakii* or *K. pneumonia* transmit at least about 90%, 95%, or 99% of incident infrared radiation having a wavenumber of between about 1300 cm$^{-1}$ and about 900 cm$^{-1}$. In certain other embodiments, membranes which are substantially transparent to infrared radiation will include materials which transmit 90%, 95%, or about 99% of incident infrared radiation except for infrared radiation which is absorbed by C—H bond stretching (e.g., IR radiation having a wavenumber of about 3000-2800 cm$^{-1}$).

In certain microporous hydrophilic polyethylene membranes provided herein, the membrane has a baseline transmittance of at least 95 percent for infrared radiation having a wavenumber of between about 1400 cm$^{-1}$ and about 750 cm$^{-1}$. More preferably, the microporous hydrophilic polyethylene membrane has a baseline transmittance of at least 99 percent for infrared radiation having a wavenumber of between about 2800 cm$^{-1}$ and about 1500 cm$^{-1}$, and between about 1450 cm$^{-1}$ and about 750 cm$^{-1}$.

Certain other microporous hydrophilic polyethylene membranes have a thickness of between about 1 micron and about 500 microns, between about 10 microns and about 100 microns, between about 45 microns and about 60 microns, or between about 50 microns and about 55 microns. Certain microporous hydrophilic polyethylene membranes have a thickness of about 40 microns, about 45 microns, about 50 microns, about 52 microns, about 54 microns, about 56 microns, about 58 microns, or about 60 microns.

In yet other microporous hydrophilic polyethylene membranes of the invention, the membrane has a porosity (e.g., a void volume) of at least about 20%, of at least about 50%, or of at least about 60%. In certain microporous hydrophilic polyethylene membranes, the porosity is at least about 60%, about 70%, or about 80%. In certain other microporous hydrophilic polyethylene membranes, the porosity of the membrane is between about 60% and about 90%.

In yet other microporous hydrophilic polyethylene membranes provided herein, the microporous polyethylene membrane has a plurality of interconnected pores. Typically the porosity of the microporous polyethylene membrane will be at least about 50% or between about 60% and about 90%. In certain microporous hydrophilic polyethylene membranes having a plurality of interconnected pores, the membrane is fluid permeable.

In certain other microporous hydrophilic polyethylene membranes having a plurality of interconnected pores, the membrane is fluid permeable but is not permeable to particles having an average particle size of at least about 0.1 micron, about 0.5 micron or about 1 micron. In certain other microporous hydrophilic polyethylene membranes having a plurality of interconnected pores, the membrane is fluid permeable but does not permit microorganisms to traverse the membrane. Yet other microporous hydrophilic polyethylene membranes further comprises at least one microorganism deposited in the pores of the membrane.

The microporous hydrophilic polyethylene membranes provided herein can be composed of any polyethylene material including high density polyethylene, low density polyethylene, cross-linked polyethylene and combinations thereof. In certain embodiments, microporous hydrophilic polyethylene membranes are composed of linear polyethylene resins which typically possess fewer absorptions in their IR spectra. Thus, certain microporous hydrophilic polyethylene membranes suitable for use in the IR sample holders and methods of detecting bacteria, are substantially composed of linear polyethylene and are substantially free of branching (e.g., free of carbon atoms having three other carbon atoms attached thereto).

In another aspect, the invention provides microporous hydrophilic polymeric membranes which is transparent to IR radiation, which membranes are prepared by a process comprising the steps of: (a) providing a microporous hydrophobic membrane which is transparent to IR radiation; and (b) contacting the hydrophobic membrane with an oxidizing plasma to produce the microporous hydrophilic membrane which is transparent to IR radiation.

Suitable microporous hydrophobic polymeric membranes which are transparent to IR radiation include membranes composed of any polymer or polymer blend which has a IR spectrum which is substantially free of absorbances over a range of wavenumber in which a measurement will be taken. Thus, certain suitable microporous hydrophobic polymeric membranes are substantially IR transparent for at least a portion of the IR spectral range (e.g., at least a portion of radiation having a wavenumber of between about 4000 cm$^{-1}$ to about 20 cm$^{-1}$). Certain microporous hydrophobic polymeric membranes which can be used in the methods of forming microporous hydrophilic polymeric membranes are disclosed in U.S. Pat. No. 5,470,747 issued to Gagnon, which is incorporated herein by reference in its entirety. In certain embodiments, microporous hydrophobic polymeric membranes composed of polyethylene, polypropylene, or poly(tetrafluoroethylene) are suitable for plasma modification.

Microporous hydrophobic polyethylene membranes are preferred, in certain embodiments, for plasma modification to form the IR-transparent microporous hydrophilic polyethylene membranes provided herein.

Although it is believed that any microporous polymeric film may be used as a sheet in the sample holder to provide some of the advantages of the invention, the sheet should be selected to reduce spectral interference of the inherent absorbances of the polymer with the bands being analyzed in the sample. Although each film has characteristic absorbances, the absorbances may be in regions of the infrared spectrum that do not interfere with the absorbances of the sample. In other words, the microporous sheet preferably exhibits relatively low absorbance, i.e., is highly transmissive, in the spectral region(s) of interest. For instance, as discussed below, except for the region of about 3000 to about 2800 $cm^{-1}$ where its aliphatic carbon-hydrogen stretching is evident as strong absorbances, sheets of polyethylene may be used in sample holders of the invention to perform infrared spectroscopic analysis across the range of about 4000 to about 20 $cm^{-1}$. Polyethylene exhibits a limited number of other signals in other portions of the range, but these are typically narrow, well-defined absorbances that are easily taken into account. TEFLON™ films and KEL-F™ films (chlorotrifluoroethylene polymers and copolymers) are typically useful in the range of about 4000 to about 1500 $cm^{-1}$.

U.S. Pat. No. 4,539,256 (Shipman) discloses microporous sheet materials and methods for making same. Many of these materials may be used in sample holders of the invention. Various patents to W. L. Gore and Associates, Inc., including U.S. Pat. Nos. 3,953,566, 3,962,153, 4,096,227, 4,110,392, 4,187,390 and 4,194,041 describe the preparation of porous articles, including microporous sheets, from polytetrafluoroethylene. Many of the polymeric materials described in those patents may be used in accordance with the present invention.

Many types of microporous hydrophobic polymer sheets which are suitable for treatment with plasma to form a microporous hydrophilic polymer sheet are commercially available in a variety of polymers, thicknesses, and void volumes. Among these are ADVENT™ film, a microporous polyethylene film, available from 3M, CELGARD™ films, hydrophobic microporous polyethylene or polypropylene films available from Hoechst Celanese, Charlotte, N.C., GORE-TEX™ film, a microporous polytetrafluoroethylene film, available from W. L. Gore Associates, ZITEX™ film, a microporous polytetrafluoroethylene film, available from Norton Performance Plastics, Wayne, N.J., and DURAPORE™ film, a microporous hydrophilic film available from Millipore Products Division, Bedford, Mass. Other illustrative examples include microporous sheets of polyolefins, e.g., ethylene/propylene copolymers, polyvinylidene fluoride, polyester, and nylon. The sheet may consist essentially of one or more of the chosen polymeric films.

In certain methods of making hydrophilic microporous polymeric membranes are prepared by treating a hydrophobic microporous polymeric membrane with plasma. In certain methods, a hydrophobic polymeric membrane which is IR transparent to IR radiation having a wavenumber of between about 4000 $cm^{-1}$ and about 1500 $cm^{-1}$ or between about 1400 $cm^{-1}$ and about 750 $cm^{-1}$ is contacted with oxidizing plasma to form a hydrophilic microporous membrane which is transparent to about the same range of IR radiation as the hydrophobic membrane prior to plasma treatment. Certain hydrophilic microporous polymeric membranes are prepared by plasma treatment of microporous hydrophobic membranes composed of polyethylene, polypropylene, or poly(tetrafluoroethylene). Certain hydrophilic microporous polymeric membranes which are transparent to IR radiation having a wavenumber of between about 1400 $cm^{-1}$ and about 750 $cm^{-1}$ are prepared by plasma treatment of a hydrophobic microporous polyethylene membrane which is transparent to IR radiation having a wavenumber of between about 1400 $cm^{-1}$ and about 750 $cm^{-1}$.

In certain methods of making microporous hydrophilic membranes, which are transparent to IR radiation, an IR transparent microporous hydrophobic membrane is contacted with an oxidizing plasma. Suitable oxidizing plasmas include plasmas formed from oxygen or gaseous mixtures comprising oxygen. Oxygen plasmas are particularly useful in the methods of making the microporous hydrophilic membranes provided herein. In certain methods a low pressure plasma is used to generate hydrophilic membranes. Typically oxygen low pressure plasmas having an oxygen partial pressure of less than 10 torr are used in the methods of the invention. In certain methods, a hydrophobic microporous membrane is contacted with an oxygen plasma having an oxygen partial pressure of about 1 torr for about 1 minute to about 120 minutes at a temperature of between about 0° C. and about 100° C. In certain other methods, a hydrophobic microporous membrane is contacted with an oxygen plasma having an oxygen partial pressure of about 1 torr for about 1 minute to about 30 minutes at a temperature of between about 15° C. and about 50° C.

In certain methods of making a microporous hydrophilic polyethylene membranes which are transparent to infrared radiation with a wavenumber of between about 1400 $cm^{-1}$ and about 750 $cm^{-1}$, the method comprises the step of contacting a microporous hydrophobic polyethylene membrane which is transparent to infrared radiation with a wavenumber of between about 1400 $cm^{-1}$ and about 750 $cm^{-1}$ with a plasma. In certain methods, the plasma is preferably an oxidizing plasma such as oxygen plasmas.

The observed transmittance of the sheet is a function of sheet thickness, porosity, infrared light scattering characteristics, and composition. It may also depend in part upon the particular wavelength or wavenumber region of interest. The standard deviation (n=20) of the sheet transmittance variability, i.e., the variation in transmittance of the sheet at different locations, is preferably less than about 25 percent relative, more preferably less than about 10 percent relative. In order to ensure highly probative evaluation of sheet transmittance variability, it is typically measured at a wavenumber at which the sheet has an absorbance of about 0.7 to about 1.0 absorbance units, e.g., at the 1460 $cm^{-1}$ absorbance for polyethylene sheets. When using a dual beam (dispersive) instrument a small standard deviation in sheet variability facilitates more accurate subtraction of the absorbances of the sample holder from those of the sample on the holder. Similarly with FTIR instruments a small standard deviation in variability permits subtraction of one standard reference spectrum from those of later analyses.

The sheet may be of any size (area) sufficient to accommodate a sample applied thereto and permit mounting in the desired instrument with a suitable support member. For reasons of instrument size limitations, the size (area) of the sheet to which a sample may be applied is typically preferably small, ranging from less than 1.0 $centimeter^2$ to about 6 $centimeter^2$ per each face in many instances. It will be understood that larger or smaller sheets may be used in accordance with the invention. The increase in sensitivity of modern instruments enables the taking of spectra of very small samples, therefore small sizes of microporous sheets may be used.

Although it is believed that any microporous polymeric film may be used as a sheet in the sample holder to provide some of the advantages of the invention, the sheet should be selected to reduce spectral interference of the inherent absorbances of the polymer with the bands being analyzed in the sample. Although each film has characteristic absorbances, the absorbances may be in regions of the infrared spectrum that do not interfere with the absorbances of the sample. In other words, the microporous sheet preferably exhibits relatively low absorbance, i.e., is highly transmissive, in the spectral region(s) of interest. For instance, as discussed below, except for the region of about 3000 to about 2800 $cm^{-1}$ where its aliphatic carbon-hydrogen stretching is evident as strong absorbances, sheets of polyethylene may be used in sample holders of the invention to perform infrared spectroscopic analysis across the range of about 4000 to about 20 $cm^{-1}$. Polyethylene exhibits a limited number of other signals in other portions of the range, but these are typically narrow, well-defined absorbances that are easily taken into account. TEFLON™ films and KEL-F™ films (chlorotrifluoroethylene polymers and copolymers) are typically useful in the range of about 4000 to about 1500 $cm^{-1}$.

The importance of this criterion may be ameliorated by use of modern spectroscopic instruments that have the capacity to "subtract" background absorbances due to solvents, the cell, the atmosphere, etc. In a dispersive type instrument, the infrared beam is split into two parallel beams, one through the sample, and the second, or reference beam, through a "blank" cell. When taking a spectrum of a sample dissolved in solvent, a cell containing only pure solvent is placed in the reference beam so that the instrument can subtract the spectrum of the solvent from that of the dissolved sample. More recent advances in electronics have allowed the spectrum of the background of a blank or reference cell to be scanned and electronically stored so that it may be subtracted from sample spectra collected later.

The process of subtraction of background absorbances which may be imperfect with conventional sample holders may also be imperfect with sample holders of the invention because absorbances may not be cleanly subtracted and may interfere with the absorbances of the sample, particularly when the sample exhibits subtle absorbances which can be inadvertently masked or lost by the subtraction process. Accordingly, the microporous sheet used in the present invention is preferably selected to minimize, and more preferably eliminate, interference of the absorbances of the microporous sheet with the sample, if possible. As the IR spectra of many polymer films are well known, it is simple to choose an appropriate sheet for use in accordance with the present invention.

In another aspect, the invention provides an infrared spectroscopy cell comprising a holder having a window, and a microporous hydrophilic polymeric membrane which is transparent to IR radiation situated in the window of the frame. In certain infrared spectroscopy cells provided herein, the microporous hydrophilic polymeric membrane is composed of a polyethylene and has an IR spectrum which is transparent at wavenumbers of between about 1400 $cm^{-1}$ and about 750 $cm^{-1}$. Certain microporous hydrophilic polyethylene membranes which are suitable for use in the infrared spectroscopy cells of the invention have an infrared spectrum consisting essentially of absorption bands at 2918 and 2849 $cm^{-1}$ and two low intensity features near 1465 $cm^{-1}$ and 725 $cm^{-1}$.

FIG. 1 illustrates sample holder 10 comprising microporous sheet 12 and support member 14. Sheet 12 is preferably inert, i.e., non-reactive, with the samples to be applied thereto, including any solvents they may contain.

Sheet 12 is preferably very thin, typically being less than about 500 microns, less than about 150 microns, between about 10 microns and about 100 microns, or preferably between about 45 microns and about 60 microns, thick. Thicker films tend to lead to greater interference due to the stronger spectral absorbances of the films. Polymeric sheets used in the invention may typically have a basis weight between to about 0.03 and 1.0 grams/square meter. Sheets with lower basis weights may be used in some instances, but may tend to be too weak to support sample material. Sheets with higher basis weights may be used in some instances, but may tend to interfere undesirably with spectroscopic analysis.

The observed transmittance of the sheet is a function of sheet thickness, porosity, infrared light scattering characteristics, and composition. It may also depend in part upon the particular wavelength or wavenumber region of interest. The standard deviation (n=20) of the sheet transmittance variability, i.e., the variation in transmittance of the sheet at different locations, is preferably less than about 25 percent relative, more preferably less than about 10 percent relative. In order to ensure highly probative evaluation of sheet transmittance variability, it is typically measured at a wavenumber at which the sheet has an absorbance of about 0.7 to about 1.0 absorbance units, e.g., at the 1460 $cm^{-1}$ absorbance for polyethylene sheets. When using a dual beam (dispersive) instrument a small standard deviation in sheet variability facilitates more accurate subtraction of the absorbances of the sample holder from those of the sample on the holder. Similarly with FTIR instruments a small standard deviation in variability permits subtraction of one standard reference spectrum from those of later analyses.

The sheet may be of any size (area) sufficient to accommodate a sample applied thereto and permit mounting in the desired instrument with a suitable support member. For reasons of instrument size limitations, the size (area) of the sheet to which a sample may be applied is typically preferably small, ranging from less than 1.0 $centimeter^2$ to about 6 $centimeter^2$ per each face in many instances. It will be understood that larger or smaller sheets may be used in accordance with the invention. The increase in sensitivity of modem instruments enables the taking of spectra of very small samples, therefore small sizes of microporous sheets may be used.

Selection of a sheet for making a sample holder for a particular application will be dependent in part upon the composition of the sample and analysis to be performed thereon. Microporous sheets may be evaluated for use in particular applications in accordance with the invention by measuring the baseline transmittance or absorbance of the sheet. The transmittance ("T") is the ratio of the power of the infrared radiation that is received by the detector after passing through the sheet to the power of the infrared radiation which is incident to the sheet and is expressed in percent. Absorbance ("A") is the negative of the log of transmittance, i.e., A=log T. Polymeric films typically scatter a portion of the light incident thereto. In holders of the present invention, the average baseline of the microporous sheet in the range of about 4000 to about 400 $cm^{-1}$ is greater than about 1, preferably greater than about 10, and more preferably greater than about 50, percent transmittance. Expressed in terms of absorbance units, the sheet has an absorbance of less than about 2, preferably less than about 1, and more preferably less than about 0.3. The average baseline absorbance of a sheet is readily determined by obtaining the absorbance of the background, i.e., empty sample holder with no sheet, and the absorbance of subject sheet at about 4000 and about 400 $cm^{-1}$. The aperture opening for both the background and sheet absorbances should have equivalent dimensions. The background absorbances are then subtracted from the sheet absorbances at about 4000 and about 400 cm$^{-1}$, respectively, the resultant values are then added together and divided by 2 to obtain the average baseline absorbance.

A preferred film for sheet 12 for the methods of assaying a sample for microorganism and/or bacterial contaminants is hydrophilic microporous polyethylene. Polyethylene exhibits a relatively simple spectrum consisting of only four distinctive absorbances in the region of about 4000 cm$^{-1}$ to about 400 cm$^{-1}$ at 2918, 2849, 1465, and 721 cm$^{-1}$, the latter two being of relatively low intensity, allowing its spectrum to easily be subtracted from the sample spectra. Polyethylene having a degree of substantial crystallinity has two additional absorbances caused by the splitting of the latter two absorbances into pairs of peaks. In addition, polyethylene is inert to many chemicals, is insensitive to moisture, and provides strong, e.g., tear and puncture resistant films at low thicknesses. An illustrative example of another polymer that may be useful in sample holders of the invention, particularly where the carbon-hydrogen bond (C—H) stretching region is of significant interest, is microporous polytetrafluoroethylene (PTFE). PTFE has no absorbances above about 1500 cm$^{-1}$ so the C—H stretching region which is at about 3000 to about 2800 cm$^{-1}$ is not subject to interfering absorbances.

The support member acts as means for mounting the sample holder in a spectrometer. In a simple embodiment, as shown in FIG. 1, member 14 may be a strip or strips of pressure sensitive adhesive coated at one or more edges of one or both faces of sheet 12. The pressure sensitive adhesive enables holder 10 to be releasably mounted directly on the spectrometer (not shown) in the path of the beam (not shown). In some instances it will be desired that the adhesive be repositionable, non-outgassing, etc. Those skilled in the art will be able to readily identify and select many suitable adhesives for the desired application, e.g., heat-activated, particular tack characteristics, etc.

Figure 2:
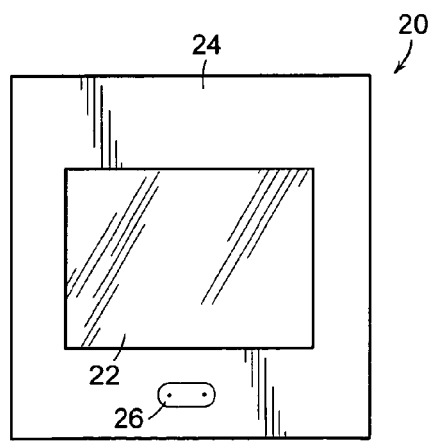
FIG. 2 is a plan view of one face of another illustrative embodiment of a sample holder of the invention.

FIG. 2 illustrates another embodiment of the invention wherein holder 20 has four edges and comprises sheet 22 and frame 24 as the support member. In this preferred embodiment, the means for mounting the sample holder comprises a frame, e.g., a photographic slide holder in which sheet 22 has been mounted as a photographic slide might have been. Frame 24 is preferably sufficiently stiff and sheet 22 mounted sufficiently tightly therein that sheet 22 is held flat across the transit opening when inserted into the spectroscopic device. As discussed above, sheet 22 is preferably very thin and thus may be subject to sagging or becoming creased or crinkled. It is important that the sheet be maintained substantially flat when the sample is in the spectroscopic device so that the IR beam passes through a constant amount of sample and to minimize the reflectance and scattering of the IR beam by the sheet which may cause interference in spectra obtained using the sample holder. The frame may be constructed of any suitable, relatively rigid material, e.g., plastic, paperboard, or metal.

In some instances it will be desirable for the prepared sample to be archived or stored for future reference. Accordingly, it is typically preferable that frame 24 be constructed of a material that may be written on or otherwise labeled so that pertinent information relating to the sample, e.g., sample or index number, may be noted thereon. Alternatively, label 26 or other additional information bearing media, e.g., microfilm, magnetic media, etc., may be included on frame 24 if desired. In some embodiments, the sample holder will further comprise a protective cover or flap (not shown) that, covers the transit opening during storage and is moved clear of the beam path during spectroscopic analysis.

The size and shape of frame 24 is dependent in part upon the sample cell receptacle of the particular spectroscopic instrument(s) in which holder 20 is to be used. Currently the industry typically uses sample holders that are about two inches wide. It has been found that standard photographic 35 millimeter slide mounts may be conveniently used as frames 24 for sample holders 20 of the invention. These slide mounts, which are typically made of plastic or paperboard, are readily available, can accommodate the microporous film and hold it flat, are sufficiently rigid, and fit easily into the sample holder mount of the instruments.

Sheet 22 may be secured in frame 24 by suitable means such as adhesive (e.g., pressure-sensitive or hot melt), sonic welding, or mechanical means. An advantage of some commercially available photographic slide mounts is that they possess adhesive, mechanical, or a combination of adhesive and mechanical mounting.

In the embodiment shown in FIG. 2, the sample may be placed on any portion of the transit opening of sheet 22, i.e., within the confines of frame 24, subject to the characteristics of the spectroscopic device being used.

Figure 3:
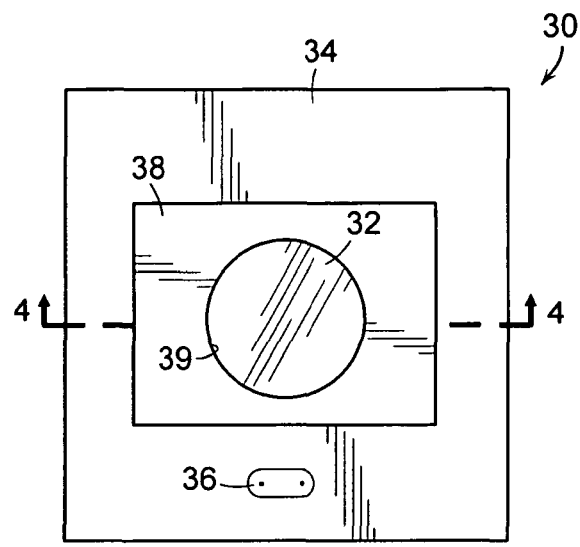
FIG. 3 is a plan view of one face of another illustrative embodiment of a sample holder of the invention comprising an aperture shield.
Figure 4:
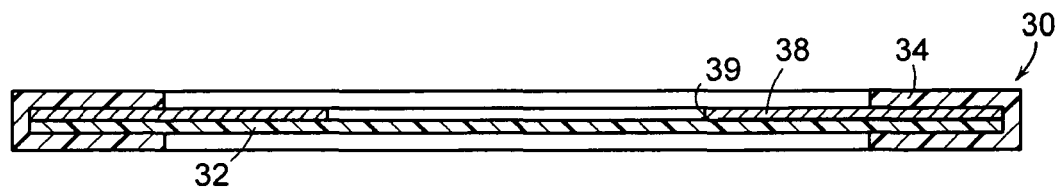
FIG. 4 is a cross-sectional view of the sample holder shown in FIG. 3 along axis 4-4.

In some instances it may be desired to restrict the area within the confines of the frame on which a sample is placed. FIG. 3 illustrates an embodiment wherein sample holder 30 comprises sheet 32 and frame 34. Holder 30 further comprises aperture shield 38 which covers a portion of sheet 32 and has transit opening 39 that leaves a portion of sheet 32 exposed on which the sample (not shown) would be placed. In use, the IR beam would pass through transit opening 39 and the sample located in opening 39. Aperture shield 38 is preferably substantially opaque to infrared light so that no interfering absorbances are produced and that incident light is not scattered. Preferably it has a transmittance in the range of about 4000 to about 400 cm$^{-1}$ of less than 10 percent and more preferably less than 1 percent. FIG. 4 illustrates holder 30 in cross-section along axis 4-4. The aperture shield may cover a portion of only one face of sheet 32 as shown on holder 30 in FIGS. 3 and 4, or it may cover portions of both faces of sheet 32, leaving at least one transit opening.

In some instances, aperture shield 38 may serve as a target to facilitate arrangement of the sample (not shown) on sheet 32 for spectroscopic analysis. In such instances, the shape, size, and location of transit opening 39 is dependent at least in part upon the characteristics of the spectroscopic device being used, particularly the geometric arrangement of the IR beam. In some instances, aperture shield 38 may serve as a small "work area" where samples can be applied to be transferred to the sheet for spectroscopic analysis. For instance, arrangement of samples of viscous materials such as plasticizers and adhesives is often facilitated by the availability of an aperture shield as a work area. Also, depending upon the configuration of frame 34 and characteristics of aperture shield 38, aperture shield 38 may impart greater stiffness of support to sheet 32.

The aperture shield may be made of the same material as the frame or other suitable material. In instances where a sample is to be processed in some fashion on the aperture shield prior to being placed on sheet 32 in transit opening 39, it is typically preferred that aperture shield not be wetted by the sample, so the sample is constrained to a small area and waste is minimized.

Aperture shield 38 may be secured with sheet 32 in frame 34 with suitable means, e.g., adhesive, sonic welding, or mechanical closures.

It will be understood that the shapes of the support member and the transit opening, and the aperture shield if used, may be of many different types, depending in part upon the construction of the holder, characteristics and specifications of the equipment with which the holder will be used, samples being analyzed, and preferences of individuals using the holder. For instance, the support member and aperture shield may be configured such that a sample holder has two or more transit openings.

The sample holders provided herein may be used with conventional "autosamplers", enabling large numbers of samples to be automatically analyzed and their spectra recorded. One such "autosampler" is Nicolet 912A0076, available from Nicolet Instruments, Madison, Wis. With such devices, a number of samples are loaded into a carousel, which automatically advances each sample holder into the infrared beam, obtains the spectrum, and then advances to the next sample. A common form of sample holder now used with such devices is a square plastic holder, approximately 5 by 5 centimeters, with a rectangular opening, approximately 2.2 by 3.5 centimeters, across which a rigid, self-supporting sample is secured. Such sample holders may be modified in accordance with the instant invention by providing a microporous sheet as described herein across the opening.

In certain other aspects, methods of assaying a test sample for bacteria or food borne pathogens by infrared spectroscopy are provided. In certain assay methods provided herein, the method comprising the steps of contacting the test sample to a hydrophilic microporous polymeric membrane which is transparent to IR radiation having a wavenumber of between about 1400 cm$^{-1}$ and about 750 cm$^{-1}$;

incubating the hydrophilic microporous polymeric membrane after applying the test sample; and measuring a test IR spectrum after incubating the hydrophilic microporous polymeric membrane;

measuring a control IR spectrum of an IR-transparent microporous hydrophilic membrane which was not contacted with a test sample;

analyzing differences between the test IR spectrum and the control IR spectrum to determine the presence of bacteria or food borne pathogens in the test sample.

In certain assay methods provided herein the food borne pathogen is a bacteria, mold, fungi, yeast, or combination thereof. In certain preferred assay methods, the assay method is suitable for detection of bacteria in a test sample by infrared spectroscopy. Certain other methods are suitable for assaying bacterial or food borne contaminants present in an aqueous test sample.

In certain other aspects, methods of assaying a test sample of aqueous bacterial suspension by infrared spectroscopy are provided in which the method comprises the steps of contacting a microporous hydrophilic polymeric membrane which is transparent to infrared radiation with a wavenumber of between about 1400 cm$^{-1}$ and about 750 cm$^{-1}$ with a test sample of aqueous bacterial suspension;

incubating the membrane after contacting with the test sample under conditions conducive to formation of bacterial colonies;

measuring a single beam IR spectrum of the bacterial colonies grown on the hydrophilic membrane contacted with the test sample;

analyzing the absorbance IR spectrum for the identification of bacterial colonies.

In certain methods of assaying a test sample for bacteria provided by the invention the test sample is a food product. Typically the food product is a liquid or powdered solid. Certain foods suitable for testing include foods comprising carbohydrates and/or proteins. Infant formula milk, either powdered infant formula milk or preformulated liquid infant formula milk, are foods suitable for testing for bacterial impurities.

The methods of assaying a test sample for bacteria by infrared spectroscopy provided herein may be used to identify the presence of any bacterial strain or other microorganism having a distinctive IR spectral feature. Preferred bacterial strains for identification include, but are not limited to, those bacteria which cause food poisoning or other diseases and disorders. Certain methods of assaying a test sample by infrared spectroscopy are particularly suitable for identification of bacteria classified in Enterobacter genus or in *Klebisella* genus. In certain other methods provided herein, samples are assayed for the presence of *Enterobacter sakazakii*, *Klebsiella pneumonia*, or combinations thereof.

The methods of assaying test samples for bacteria by IR spectroscopy comprise a step of contacting the test sample to a hydrophilic microporous polymeric membrane which is transparent to IR radiation. Any method of delivering at least a portion of the test sample, e.g., a solution or suspension of a food product or an aqueous bacterial suspension, to the hydrophilic microporous polymeric membrane which does not result in degradation or destruction of bacteria present in the sample is suitable for use in the assay methods provided herein. In certain assay methods, the test solution is contacted with the hydrophilic microporous polymeric membrane by filtration of the test sample through the membrane or by microarray printing of a test to sample aqueous solution or aqueous suspension onto at least a portion of the surface of the membrane. Typically, when the test sample is a solid, it is first dissolved or suspended in a aqueous medium prior to contacting the test sample with the membrane.

In certain assay methods of the invention, the incubation step comprises contacting at least a portion of the membrane with a culture media. Any culture media including liquid media and solid media may be used in the methods of the invention. In certain embodiments, depositing the membrane on the surface of a solid culture media allows for immediate post-incubation infrared spectroscopic analysis of membrane. Typically preferred culture media include solid agar media.

The incubation step is typically carried out at a temperature conducive to bacterial growth for at least one hour. In certain methods the incubation step is conducted at between about 10° C. and about 45° C., between about 15° C. and about 45° C. or between about room temperature and about 40° C. Certain methods of the invention include an incubation step conducted at about 35° C., about 36° C., about 37° C., about 38° C., or at about 39° C. Typically the microporous membrane is contacted with the culture media for between about 10 minutes and about 48 hours, or for between about 1 hour and about 48 hours. in certain methods, the incubation step lasts for between about 2 hours and about 12 hours.

The method of assaying samples for bacterial contaminants provides a method complimentary to other FDA promulgated methods of identifying bacterial contaminants in food stuffs.

The methods of the present invention provide the capability of direct measurement of bacterial microcolonies growing on a plasma treated hydrophilic microporous polyethylene membrane by infrared spectroscopy. Thus, infrared images of intact bacterial microcolonies are provided (FIGS. 5A and 5B) and IR spectra for intact bacteria were obtained by inoculating an IR-transparent hydrophilic microporous polyethylene membrane of the invention on a solid BHI agar medium after contacting the membrane with a solution containing bacteria. The numbers of isolated microcolonies found for test samples of *E. sakazakii, K. pneumoniae*, or a mixture of both were approximately in the order of $10^2$ and $10^1$ at the $1:10^7$ and $1:10^8$ dilution levels, respectively. IR spectra of microcolonies (FIG. 6) of *E. sakazakii* or *K. pneumonia* were sequentially recorded for the various test samples, namely those that had been inoculated with each bacterium as well as their mixture. The spectral region spanning the observed spectral range was considered; however, the optimal region for differentiation between the two microorganisms was 1172-995 cm$^{-1}$ (FIG. 6), and was used to discriminate between the two bacteria (FIG. 7). An HCA dendrogram illustrating the successful differentiation of a mixture of colonies of *E. sakazakii* and *K. pneumonia* measured by IR microspectroscopy is shown in FIG. 7. HCA groups data into clusters having similar attributes, and the dendrogram is a visual presentation of the clustering. Distances between pairs of samples are calculated and compared. Similar samples will be separated by relatively small distances (left side of the dendrogram) while dissimilar samples will be separated by relatively large distances (right side of the dendrogram). Euclidian distances and centroid linkage method were used to generate the dendrograms presented in this work. An index at the top of each dendrogram is an arbitrary scale used to compare similarities at different distances.

Inspection of FIG. 7 indicates that there is complete separation of the spectral data into two main clusters for *E. sakazakii* and *K. pneumonia*. IR data observed *E. sakazakii* and *K. pneumonia* colonies obtained for test samples inoculated with mixtures of the two organisms also clustered in one of the two groups (FIG. 7), and identified as presumptive *E. sakazakii* or *K. pneumonia* colonies. The colony-to-colony variability was much smaller than the between-microorganism variability, thus meeting the fundamental requirement for reliable presumptive bacteria identification by infrared microspectroscopy.

In certain assay methods, it is desirable to rapidly screen large numbers of samples. Applicants have discovered a method of applying test samples to a IR-transparent hydrophilic microporous membrane of the invention by high-throughput microarray printing. Methods of depositing liquid samples onto a porous membrane have been reported in *Foodborne Pathog Dis* (2004) 1 (3):172-7; *Appl Spectrosc* (2004) 58 (11):1364-8; *Applied Spectroscopy* (2005) 56 (6):732-736; and *Vibrational Spectroscopy* (2005) 38:229-235. In the methods of the invention, diluted pre-enriched infant formula milk (IFM) test samples are reproducibly deposited onto IR transparent hydrophilic microporous polyethylene membranes by microarray printing (see, Example 5). The size of the arrayed colonies formed by microarray printing varies. That is, colonies that originated from higher concentration bacterial suspensions are larger than more dilute suspensions. For example, colonies formed by printing a suspension that had been diluted to $1:10^3$ are approximately 200 μm in diameter, whereas those colonies formed by printing a suspension that had been diluted to $1:10^2$ are larger (approximately 0.5 mm in diameter). Observed IR spectra clustered into two groups as demonstrated in the dendrogram in FIG. 8. Therefore, the application of microarray printing on IR-transparent hydrophilic microporous polyethylene membranes of the invention is an efficient tool to rapidly survey and presumptively identify the presence of a pathogen such as *E. sakazakii* in a large number of IFM and other food products by infrared spectroscopic methods of the invention.

EXAMPLES

It should be appreciated that the invention should not be construed to be limited to the example which is now described; rather, the invention should be construed to include any and all applications provided herein and all equivalent variations within the skill of the ordinary artisan.

Example 1

Organisms and Growth Conditions

Isolates from *E. sakazakii*, and *K. pneumoniae* are obtained from the Food and Drug Administration, Center for Food Safety and Applied Nutrition culture collection. The stock cultures are streaked onto Brain Heart Infusion (BHI) agar plates and incubated at 37° C. for approximately 24 hr.

Example 2

Inoculation and Pre-enrichment

Infant formula milk (IFM) products are locally purchased. Because of the low incidence of *E. sakazakii* in IFM products, samples are inoculated during pre-enrichment at levels that are similar to those that have been reported (*J Clin Microbiol* (1988) 26 (4):743-6) to be found in some commercial IFM products. *E. sakazakii* is inoculated from dilutions estimated to to give *E. sakazakii* levels of 1 CFU/100 g into an IFM sample that consisted of a 10 g portion dissolved in 90 ml of pre-warmed to 45° C. sterile distilled water. The inoculated IFM sample in water is pre-enriched by incubating overnight at 36° C. The same procedure is repeated for *K. pneumoniae* and for the mixture of the two microorganisms used.

Example 3

Surface Ionization by Plasma Treatment of Polyethylene Membrane Filter

A Plasma Etch, Model BT-1 (Carson City, Nev.) plasma system is used to treat the microporous (porosity 0.2 μm), hydrophobic polyethylene membrane (3M, St. Paul, Minn.) that is approximately 0.002 inch or 51 μm thick. Each side of the membrane surface (area approximately 9"×11") is plasma-treated at room temperature with low pressure (below ~1 torr) oxygen, at a flow rate of 60 cc/min, for 5 min.

Example 4

Figure 5A:
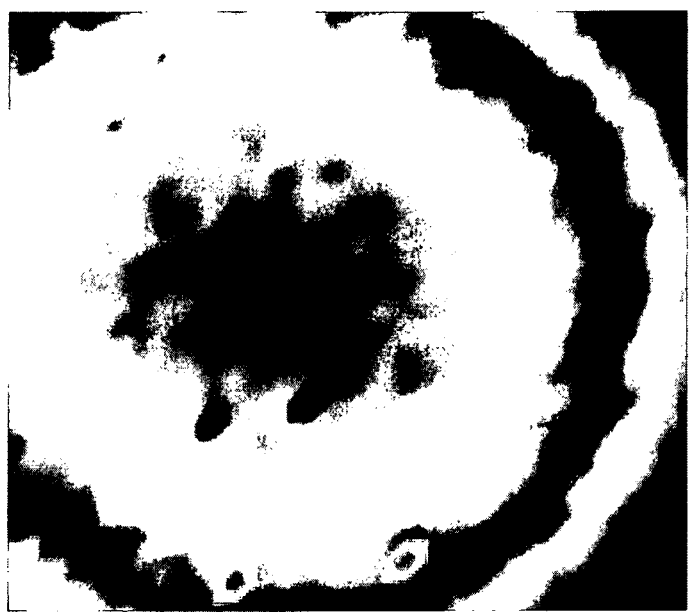
FIG. 5 is an image of an intact bacterial microcolony incubated on a disposable, microporous, plasma-treated, hydrophilic, IR-transparent polyethylene substrate indicating (A) a diameter of approximately 250 μm, and (B) a hemispherical topology, wherein the image was obtained by infrared spectroscopy.
Figure 5B:
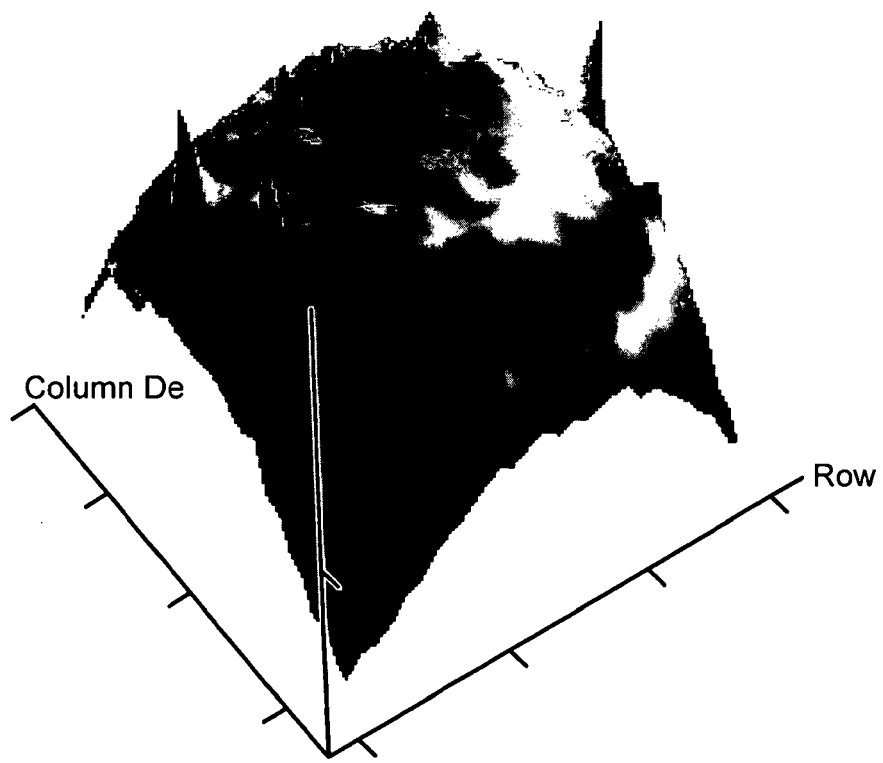

Filtration and Incubation of Bacterial Cells and Growth of Microcolonies on Plasma-treated Polyethylene Membrane The pre-enriched IFM test samples of *E. sakazakii, K. pneumoniae*, or a mixture of both are each serially diluted to $1:10^9$. Each of the 100 μl portions of the $1:10^7$ and $1:10^8$ serially diluted samples is slowly dispensed over a 0.5"×0.5" area of a 1"×1" plasma-treated, hydrophilic polyethylene membrane and filtered under vacuum. These samples are used because the number of isolated microcolonies generated is approximately in the order of $10^2$ and $10^1$ at the $1:10^7$ and $1:10^8$ dilution levels, respectively. Each polyethylene membrane on which isolated bacterial cells are filtered is placed on BHI agar media and incubated at 36° C. for 4-6 hrs until the formation of microcolonies (with a diameter of approximately 200 μm or more) is observed (FIG. 5A and 5B). Upon placing the polyethylene membrane filter on agar, it immediately appears to be wet. The wet polyethylene membrane on which isolated colonies are observed after incubation is carefully removed from the agar medium and rapidly (15 sec)

placed flat between the two sides of a film holder fabricated with masking tape. The holder is a square of approximately 1.5 inch (about 3.75 cm) on each side with a frame width of approximately 0.6 inch (about 1.5 cm). This step is necessary to keep the polyethylene substrate in a stretched and flat configuration, and has to be carried out rapidly because the thin membrane would otherwise curl upon removal from the agar medium as it dries at room temperature in approximately 15 seconds.

Example 5

Microarray Printing on Plasma-treated Polyethylene Membrane

Aliquots of the pre-enriched IFM test samples of *E. sakazakii*, *K. pneumoniae*, or a mixture of both are each diluted to 1:$10^2$ and 1:$10^3$. Portions (30 µl) from the various diluted suspensions of each sample are transferred to a microtiter plate which is placed in a PixSys 5000 contact micro-spotting robotic system (Cartesian Technologies, Inc., Irvine, Calif.). Using a CMP10B micro-spotting pin (Arraylt-TeleChem International, Inc. Sunnyvale, Calif.), the suspensions are printed on a 1"×3" section of the plasma-treated, hydrophilic polyethylene membrane after placing it over a zinc selenide slide of similar dimensions that served only as a solid support during printing. For each test sample, a 600-nL uptake volume of bacterial cell suspension is taken by the micro-spotting pin from one of the 384 microtiter plate wells, and five 5.2-nL replicate droplets are sequentially printed on the surface of treated polyethylene membrane. After printing five replicates of each test sample, the pin is cleaned automatically using water and vacuum three times. The polyethylene membrane, on which a microarray of dilute bacterial suspensions is printed, is subsequently placed on BHI agar media and incubated at 36° C. for 3-4 hrs until the formation of a microarray of microcolonies is observed.

Example 6

FTIR Microspectroscopy with Single-point MCT Detection

Figure 6:
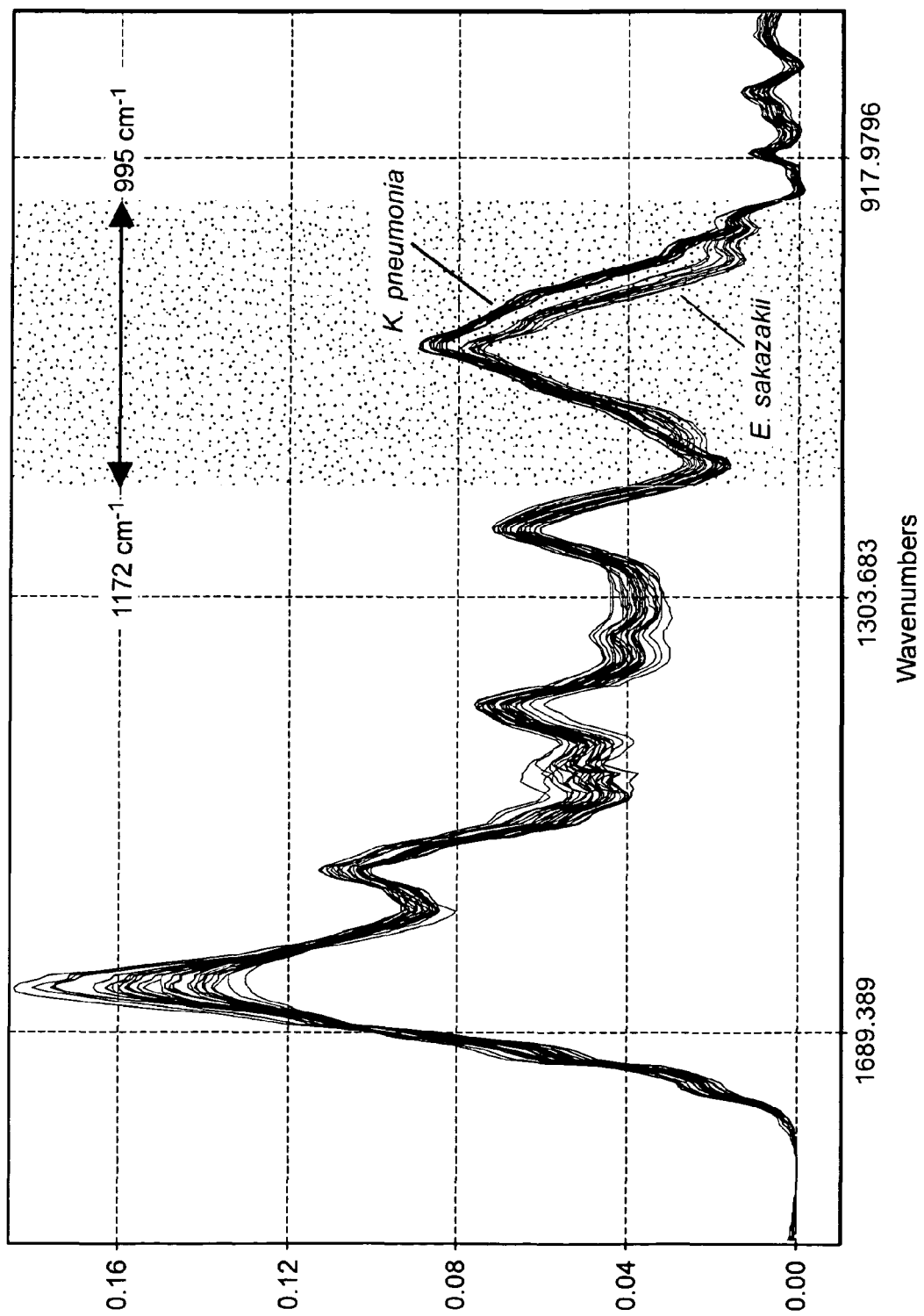
FIG. 6 is a plot of 28 Fourier transform infrared spectroscopy (FTIR) spectra (1172-995 cm$^{-1}$) obtained by measuring a microcolony of *E. sakazakii* or *K. pneumonia* from infant formula milk (IFM) test samples inoculated with one or both of them.

A Magna 550 FTIR spectrometer equipped with a Continuµm™ infrared microscope (Thermo, Madison, Wis.) and a 0.25-mm mercury-cadmium-telluride (MCT) detector is employed to record the Fourier transform (FT) IR spectra of air-dried microcolonies observed on the plasma-treated polyethylene substrate. FTIR spectra are collected over a wavenumber range of 4000 to 600 $cm^{-1}$ at a resolution of 8 $cm^{-1}$. The polyethylene spectrum consists of an intense feature due to hydrocarbon stretching vibrations in the range 2940-2840 $cm^{-1}$, and two weak deformation bands near 1465 and 725 $cm^{-1}$. These bands fall outside the frequency range of 1172-995 $cm^{-1}$ that is used to discriminate between the two bacteria in the present study (see FIG. 6). To enhance the signal-to-noise ratio, 64 scans are co-added (approximately 1 min) and signal averaged for each micro-spot using a 100 µm×100 µm aperture. The estimated signal-to-noise ratio is about 5000:1. A reference background spectrum is measured from a clear portion of the polyethylene substrate with no bacterial colonies. Each of the displayed 28 FTIR spectra in FIG. 6 is obtained by measuring a microcolony of *E. sakazakii* or *K. pneumonia* from infant formula milk (IFM) test samples inoculated with one or both of the bacterial lines by the method of Example 2. The wavenumber region of 1172-995 $cm^{-1}$ exhibits unique spectral features for microcolonies of *E. sakazakii* and *K. pneumonia* and is therefore useful in discrimination between *E. sakazakii* and *K. pneumonia*.

IR chemical images of an intact bacterial microcolony obtained after incubation on a disposable, microporous, plasma-treated, hydrophilic, IR-transparent polyethylene substrate indicating (FIG. 5A) a diameter of approximately 250 µm, and (FIG. 5B) a hemispherical topology. Images are obtained using a Varian (Randolph, Mass.) FTS 7000 e IR spectrometer interfaced to a Varian UMA 600 IR microscope equipped with a Schwarzschield 15X Cassegrain objective and a 32×32 focal plane array MCT detector. Images are generated by plotting the intensity at 1223 $cm^{-1}$ for a colony obtained from a six-month-old archived sample that had been produced by the filtration and incubation-over-agar procedure (see Example 5). The background was recorded from an adjacent colony-free region of the treated polyethylene substrate.

For each image acquisition, a total of 1024 FTIR spectra were collected simultaneously by co-adding 16 scans at a resolution of 8 $cm^{-1}$ between 4000 and 900 $cm^{-1}$.

Example 7

Data Analysis and Presumptive Identification of Microcolonies

The acquired FTIR spectra are imported as absorbance (*.SPC) files into the multivariate statistics program PIROUETTE™ 3.11 (InfoMetrix, Inc., Woodinville, Wash.). Spectral data are transformed by baseline correction and normalization. The Hierarchical Cluster Analysis (HCA) algorithm is used for visual elucidation of clustering; dendrograms are computed using centroid linkage and Euclidean distances as the metric (Kowalski, B. 1983. Chemometrics: Mathematics in Statistics and Chemistry., edited by NATO. Boston: D. Reidel Publishing Co and Massart, et al., 1988. Data Handling in Science and Technology. In *Chemometrics: textbook*. New York: Elsevier).

The foregoing description of the invention is merely illustrative thereof, and it is understood that variations and modifications can be effected without departing from the spirit or scope of the invention as set forth in the following claims. Each of the documents referred to herein are incorporated by reference into the disclosure of the application.

All documents mentioned herein are incorporated herein in their entirety by reference.

What is claimed is:

1. An infrared spectroscopy cell for use in direct detection of bacteria comprising:
   a holder having a window and a frame; and
   a microporous hydrophilic polyethylene membrane situated in the window of the frame, wherein the microporous hydrophilic polyethylene membrane transmits at least 90% of infrared radiation (IR) and has an IR spectrum consisting essentially of absorption bands at 2918 and 2849 $cm^{-1}$, as well as two pairs of low intensity features near 1465 and 725 $cm^{-1}$.

2. The infrared spectroscopy cell of claim 1, wherein the microporous hydrophilic polyethylene membrane transmits at least 95% of IR.

3. The infrared spectroscopy cell of claim 2, wherein the at least 95% of transmitted IR has a wavenumber of between 1400 $cm^{-1}$ and 750 $cm^{-1}$.

4. The infrared spectroscopy cell of claim 1, wherein the microporous hydrophilic polyethylene membrane transmits at least 99% of IR.

5. The infrared spectroscopy cell of claim 4, wherein the transmitted IR has a wavenumber of between 2800 cm$^{-1}$ and 1500 cm$^{-1}$ and between 1400 cm$^{-1}$ and 750 cm$^{-1}$.

6. A method of assaying a test sample of aqueous bacterial suspension, the method comprising:
- adding the test sample of aqueous bacterial suspension to the infrared spectroscopy cell of claim 1;
- incubating the membrane after contacting with the test sample under conditions conducive to formation of bacterial colonies;
- measuring a single beam IR spectrum of the bacterial colonies grown on the hydrophilic membrane contacted with the test sample; and
- analyzing the absorbance IR spectrum for the identification of bacterial colonies.

\* \* \* \* \*